US00PP28442P3

(12) United States Plant Patent
Bradford et al.

(10) Patent No.: US PP28,442 P3
(45) Date of Patent: Sep. 26, 2017

(54) PLUM TREE NAMED 'PLUMCANDY XII'

(50) Latin Name: *Prunus salicina*
Varietal Denomination: Plumcandy XII

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 26 days.

(21) Appl. No.: 14/757,247

(22) Filed: Dec. 11, 2015

(65) Prior Publication Data

US 2017/0172023 P1 Jun. 15, 2017

(51) Int. Cl.
*A01H 5/08* (2006.01)

(52) U.S. Cl.
USPC ..... Plt./184

(58) Field of Classification Search
USPC ..... Plt./184
See application file for complete search history.

(56) References Cited

U.S. PATENT DOCUMENTS

PP14,220 P2 10/2003 Bradford
PP23,740 P3 7/2013 Bradford

*Primary Examiner* — Keith Robinson

(57) ABSTRACT

The present invention relates to a plum tree and more particularly to a new and distinct variety broadly characterized by a large size, vigorous, hardy, and very productive tree. Being self-unfruitful, the present variety requires cross pollination from another plum or interspecific tree that blooms during the mid to late season, such as 'Plumsweet IV' interspecific tree (U.S. Plant Pat. No. 16,461). The present variety's abundance of blossoms and pollen entices strong bee activity to facilitate pollination. The fruit matures under the ecological conditions described during the first week of October, with first picking on Oct. 1, 2015. The fruit is uniform, very large in size, nearly full red in skin color, freestone in type, pure yellow in flesh color, firm in texture, juicy, and very good in flavor.

1 Drawing Sheet

Botanical classification: *Prunus salicina.*
Variety denomination: 'PLUMCANDY XII'.

BACKGROUND OF THE VARIETY

In a continuing effort to improve the quality of shipping fruits, we, the inventors, typically hybridize a large number of peach, nectarine, plum, apricot, and cherry seedlings each year. We also grow a lesser number of open pollinated seeds of each of these fruits. The present invention relates to a new and distinct variety of plum tree, which has been denominated varietally as 'Plumcandy XII'.

During a typical blooming season we isolate as seed parents both individual and groups of different plum trees by covering them with screen houses. A hive of bees is placed inside each such house, and bouquets to provide pollen from different plum, apricot, and interspecific hybrid trees are placed in buckets near the trees approximately every two days for the duration of the bloom. During 2007 one such house containing 'September Yummy' plum tree (U.S. Plant Pat. No. 14,220) was crossed by us in this manner. To pollinate this plum tree, we selected bouquets from several sources of plum trees without keeping specific written details. Upon reaching maturity the fruit from this plum tree was harvested, and the seeds were removed, cracked, stratified and germinated as a group with the label "H12". They were grown as seedlings on their own root in our greenhouse and upon reaching dormancy transplanted to a cultivated area of our experimental orchard located near Le Grand, Calif. in Merced County (San Joaquin Valley). During the summer of 2011 the claimed variety was selected by us as a single plant from the group of seedlings described above. Subsequent to origination of the present variety of plum tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is most similar to its seed parent, 'September Yummy' (U.S. Plant Pat. No. 14,220) plum, by having a large, vigorous, and very productive tree, by blooming in the mid to late season, by being self-unfruitful, and by producing plums that are fairly globose in shape, nearly full red in skin color, very good in flavor, juicy, and firm in texture, but is distinguished therefrom by producing plums that are much larger in size, by having full yellow flesh color without red bleeding near the skin, and that ripen about twenty days later.

The present variety is also similar to 'Latesweet XX' interspecific tree (U.S. Plant Pat. No. 23,740), by being self-unfruitful, by blooming in the mid to late season, and by producing fruit that is full red in skin color, yellow in flesh color, firm in texture, juicy, freestone in type, and sweet in flavor, but is distinguished therefrom by producing fruit that is much larger in size, that is globose instead of oblate in shape, and that matures about fifteen days earlier.

SUMMARY OF VARIETY

The present plum variety is characterized by a large size, vigorous, hardy, and very productive tree. Being self-unfruitful, the present variety requires cross pollination from another plum or interspecific tree that blooms during the mid to late season, such as 'Plumsweet IV' interspecific tree (U.S. Plant Pat. No. 16,461). The present variety's abundance of blossoms and pollen entices strong bee activity to facilitate pollination. The fruit matures under the ecological conditions described during the first week of October, with first picking on Oct. 1, 2015. The fruit is uniform, very large in size, nearly full red in skin color, freestone in type, pure yellow in flesh color, firm in texture, juicy, and very good in flavor.

DRAWING

The accompanying photograph exhibits four whole fruits positioned to display the characteristics of the skin color and form, one divided fruit to reveal the flesh and stone, typical leaves, and two insets depicting the flower buds and blossoms as they appeared on the tree during the blooming season.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin Valley), Calif., and was developed at the state of shipping ripe on Oct. 8, 2015, on the original tree during its eighth growing season. All major color code designations are by reference to the Inter-Society Color Council, National Bureau of Standards. Common color names are also used occasionally.

It is to be noted that the 2015 fruit season in California was very warm during the spring and the ripening times of almost all varieties were about twenty days earlier than other years.

TREE

Size: Large, reaching and maintaining a height of 15' [4.57 m.] and a spread of 9' [2.74 m.] after eight growing seasons utilizing typical dormant pruning.

Vigor: Vigorous, responding typically to irrigation and fertilization. The variety grows about 4' [1.22 m.] of surplus top-growth during the spring and summer. The plant should be grown on a standard commercial rootstock for production purposes.

Growth: Upright and dense.

Form: Pruned to a Central Leader type.

Hardiness: Hardy with respect to central California winters.

Heat tolerance: Observed to perform adequately in typical central California climatic conditions, which typically include prolonged periods of heat.

Drought tolerance: Variety is developed for commercial orchards and requires regular irrigation.

Production: Very productive, thinning usually necessary.

Fertility: Self-unfruitful, requiring cross pollination by a suitable mid to late seasonal blooming plum or interspecific, such as 'Plumsweet IV' interspecific tree (U.S. Plant Pat. No. 16,461).

Bearing: Regular bearer, weather dependent, no crop failures observed as of yet.

Trunk:

*Size*.—Stocky, reaching a maximum diameter of 5" [127 mm.] after the eighth growing season.

*Texture*.—Medium roughness.

*Bark color*.—A Grayish brown [61. gy.Br] and Dark grayish brown [62. d.gy.Br] variegation with Light grayish yellowish brown [79. l.gy.yBr] crevices present.

*Lenticels*.—Approximate Number Per Square Inch: 6. Color: Deep orange [51. deep O]. Typical Size: ¼" [6.4 mm.] in length. The width is typically one fourth as much as the length. Shape: Eye-shaped.

Branches:

*Size*.—Diameter of lowest hanger is 1¼" [31.8 mm.] measured 6" from the central leader.

*Texture*.—Smooth on first and second year wood, increasing roughness with age.

*Color*.—1st Year Wood Topside: Grayish red [19. gy.R]. 1st Year Wood Underside: Strong yellow green [117. s.YG]. Older Wood: A Light brownish gray [63. l.brGy] and Dark brown [59. d.Br] variegation.

*Lenticels*.—Approximate Number Per Square Inch: 10. Color: Light yellowish brown [76. l.yBr]. Typical size: Small, 1/32" [0.8 mm.] in length. The width is typically one fourth as much as the length. Shape: Eye-shaped.

Leaves:

*Size*.—Medium. Average Length: 4⅛" [104.8 mm.]. Average width: 1 15/16" [49.2 mm.].

*Arrangement*.—Alternate.

*Thickness*.—Medium.

*Form*.—Elliptical.

*Apex*.—Acuminate.

*Base*.—Acute with an average angle base angle of seventy degrees.

*Surface*.—Smooth on both sides.

*Color*.—Dorsal Surface: Moderate olive green [125. m.OlG]. Ventral Surface: Moderate yellow green [120. m.YG].

*Margin*.—Finely serrate.

*Venation*.—Pinnately net veined.

*Petiole*.—Average Length: 15/16" [23.8 mm.]. Average Thickness: 1/16" [1.6 mm.]. Color: Moderate greenish yellow [102. m.gY] with Grayish reddish orange [39. gy.rO] where exposed to sunlight.

*Stipules*.—Number: 2 per leaf, up to 6 per growing tip. Average Length: ¼" [6.4 mm.]. Color: Brilliant yellow green [116. brill.YG] becoming Dark grayish reddish brown [47. d.gy.rBr] with age.

*Glands*.—Number: 1 to 4, most often 2. Position: Usually alternate, positioned mostly on the petiole. Form: Globose. Size: Small, 1/64" [0.4 mm.] in diameter. Color: Moderate greenish yellow [102. m.gY] becoming Dark grayish reddish brown [47. d.gy.rBr] in the center with age.

*Leaf buds*.—Pointed.

Flower buds:

*Hardiness*.—Hardy, with respect to central California blooming season.

*Diameter*.—Typically 3/16" [4.8 mm.] 1 week before bloom.

*Length*.—Typically ⅜" [9.5 mm.] 1 week before bloom.

*Form*.—Not appressed.

*Surface*.—Slightly pubescent.

*Color*.—White [263. White].

Flowers: Perfect, complete, perigynous, usually a single pistil, about twenty-eight stamens, five sepals and petal locations alternately positioned.

*Average flower diameter.*—1 1/16" [27.0 mm.].
*Average flower depth.*—3/8" [9.5 mm.] when fully open.
*Average pedicel length.*—3/16" [4.8 mm.].
*Number of petals.*—Five, no double blossoms observed.
*Petal shape.*—Oval.
*Petal margin.*—Entire, somewhat wavy.
*Average petal diameter.*—7/16" [11.1 mm.].
*Average petal length.*—1/2" [12.7 mm.].
*Petal apex.*—Rounded.
*Petal base.*—Rounded.
*Petal color.*—White [263. White] on both sides.
*Anther color.*—Light orange yellow [70. l.OY].
*Pollen production.*—Abundant, bee enticing.
*Pollen color.*—Strong yellow [84. s.Y].
*Stigma color.*—Light greenish yellow [101. l.gY].
*Stigma position.*—Stigma is located slightly below the surrounding anthers.
*Sepal color.*—Brilliant yellow green [116. brill.YG] on both sides.
*Sepal length.*—3/16" [4.8 mm.].
*Sepal width.*—5/32" [4.0 mm.].
*Sepal apex.*—Rounded to elliptical to match the width and length.
*Average pistil length.*—1/2" [12.7 mm.].
*Average stamen length.*—7/16" [11.1 mm.].
*Ovary.*—Smooth.
*Fragrance.*—Moderate.
*Blooming period.*—Medium to late compared with other varieties, about 2 days after 'Santa Rosa' plum (unpatented).
*Onset of bloom.*—One percent on Feb. 20, 2015.
*Date of full bloom.*—Mar. 1, 2015.
*Duration of bloom.*—One to two weeks, dependent on ambient temperature.
*Bloom density.*—Heavy.
*Number per cluster.*—Typically 3 or 4, up to 8 observed.

FRUIT

Maturity when described: Shipping ripe, Oct. 8, 2015.
Date of first picking: Oct. 1, 2015.
Date of last picking: Oct. 20, 2015.
Size: Uniform, very large.

*Average diameter axially.*—2 3/4" [69.9 mm.].
*Average diameter across suture plane.*—2 13/16" [71.4 mm.].
*Average diameter across cheek plain.*—2 3/4" [69.9 mm.].
*Typical weight.*—6.8 ounces [193 grams].

Form: Uniform, mostly symmetrical, globose.

*Longitudinal section form.*—Round to oval.
*Transverse section through diameter.*—Round.

Suture: A very shallow trough extending from the base to the apex.
Ventral surface: Rounded, very slight lipping toward the base.
Lips: Fairly equal.
Cavity: Flaring, circular, suture showing on one side.

*Depth.*—7/16" [11.1 mm.].
*Breadth.*—1 1/4" [31.8 mm.].

Base: Truncate, somewhat cordate when viewed parallel to the suture.
Apex: Rounded.
Pistil point: A Light yellow [86. l.Y] inconspicuous dot.
Stem: Medium size.

*Average length.*—3/8" [9.5 mm.].
*Average width.*—1/8" [3.2 mm.].

Skin:

*Thickness.*—Medium.
*Surface.*—Smooth.
*Tenacity.*—Tenacious to flesh.
*Astringency.*—Slight.
*Tendency to crack.*—None observed.
*Color.*—Dark red [16. d.R] smoothly blending to Moderate reddish orange [37. m.rO] with moderate Light yellow [86. l.Y] freckling throughout. Occasionally small Moderate yellow [87. m.Y] areas occur where completely sun protected.
*Lenticels.*—Number Per Square Inch: About 80. Average diameter: 1/48" [0.5 mm].
*Bloom.*—Moderate.

Flesh:

*Color.*—Brilliant yellow [89. brill.Y] with Pale yellow [89. p.Y] fibers throughout.
*Surface of pit cavity.*—Covered with Deep orange yellow [69. deep OY] fibers.
*Amygdalin.*—Moderate.
*Juice.*—Abundant, rich.
*Texture.*—Firm, crisp.
*Fibers.*—Abundant, tender.
*Ripens.*—Fairly even.
*Flavor.*—A tasty blend of acid and sugar, typically 18 brix.
*Aroma.*—Slight.
*Eating quality.*—Very good.

STONE

Type: Freestone.
Form: Oval.
Hilum: Narrow.
Base: Rounded.
Apex: Acute with an average angle of 80 degrees and a sharp tip 1/16" [1.6 mm.] in length.
Sides: Fairly equal.
Surface: Rough.
External color of stone: Moderate yellowish brown [77. m.yBr].
Pit wall color when cracked: Light yellowish brown [76. l.yBr].
Cavity surface color: Deep yellowish brown [75. deep yBr].
Average pit wall thickness: 1/8" [3.2 mm.].
Average length: 1" [25.4 mm.].
Average width: 5/8" [15.9 mm.].
Average breadth: 7/16" [11.1 mm.].
Tendency to split: None observed.
Kernel:

*Form.*—Oval.
*Pellicle color.*—Dark yellowish brown [78. d.yBr].
*Skin color.*—Light yellowish brown [76. l.yBr].
*Vein color.*—Moderate yellowish brown [77. m.yBr].
*Taste.*—Bitter.
*Viable.*—Yes.
*Average length.*—9/16" [14.3 mm.].
*Average width.*—3/8" [9.5 mm.].

USE

Market: Fresh market and long distance shipping.

Keeping quality: Excellent. Fruit quality observed to remain in good condition in after 30 days in standard cold room at 36° Fahrenheit [2° Celsius].

Shipping quality: Excellent.

Resistance to insects: Not tested.

Resistance to diseases: Not tested.

OTHER NOTES

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, *prunus salicina*, substantially as illustrated and described, that is most similar to its seed parent, 'September Yummy' (U.S. Plant Pat. No. 14,220) plum, by having a large, vigorous, and very productive tree, by blooming in the mid to late season, by being self-unfruitful, and by producing plums that are fairly globose in shape, nearly full red in skin color, very good in flavor, juicy, and firm in texture, but is distinguished therefrom by producing plums that are much larger in size, by having full yellow flesh color without red bleeding near the skin, and that ripen about twenty days later.

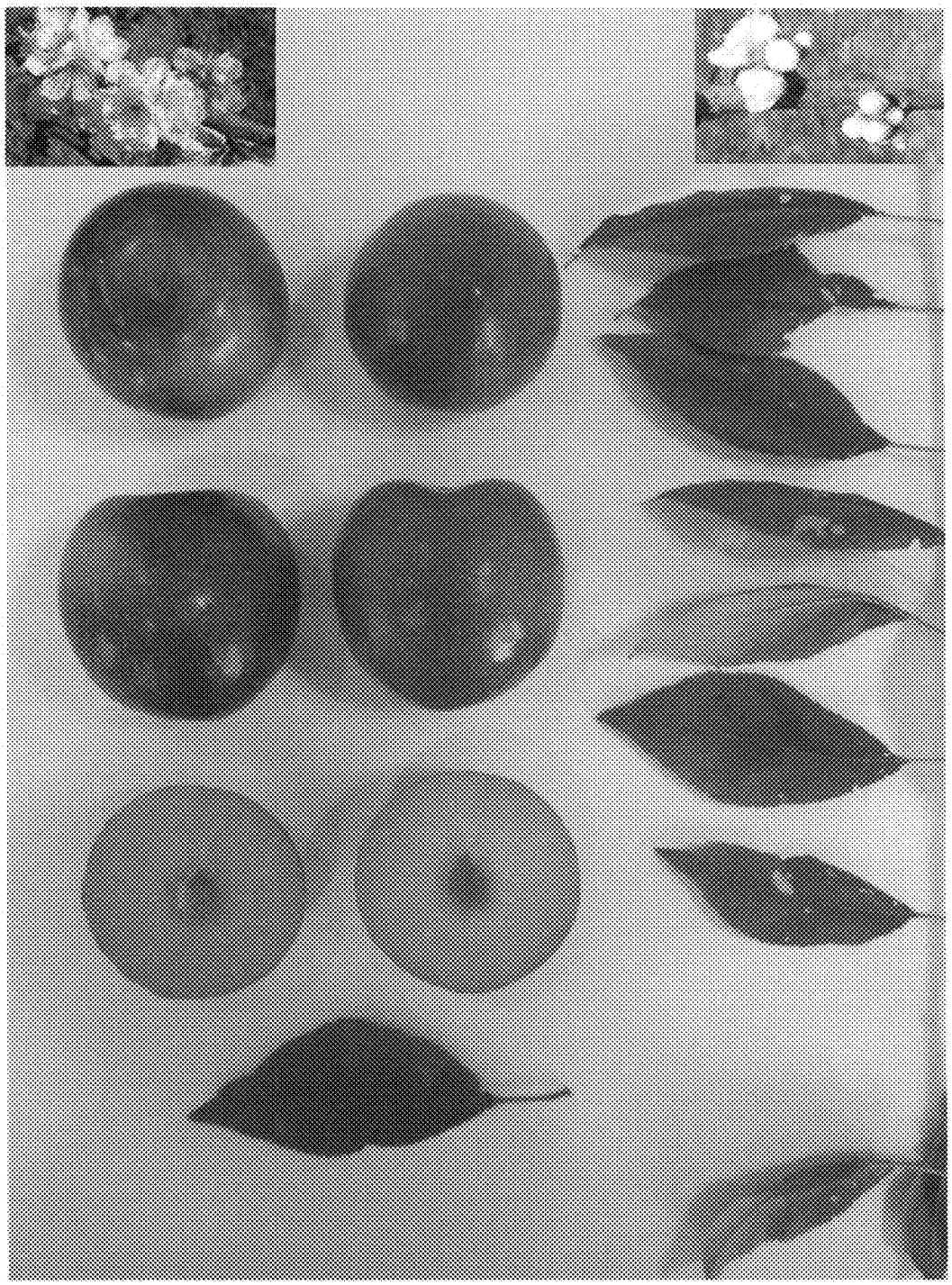

* * * * *